United States Patent [19]

Murib et al.

[11] Patent Number: 5,091,559

[45] Date of Patent: Feb. 25, 1992

[54] PROCESS FOR THE PREPARATION OF ALKYL 4-OXOBUTYRATE AND ITS ACETALS

[75] Inventors: Jawad H. Murib, Cincinnati; William D. Baugh, Wilmington, both of Ohio

[73] Assignee: Quantum Chemical Corporation, New York, N.Y.

[21] Appl. No.: 153,621

[22] Filed: Feb. 8, 1988

Related U.S. Application Data

[63] Continuation-in-part of Ser. No. 777,372, Sep. 18, 1985, abandoned, which is a continuation-in-part of Ser. No. 264,925, May 18, 1981, abandoned.

[51] Int. Cl.$^5$ .................. C07C 67/36; C07C 67/37; C07C 69/716
[52] U.S. Cl. .................... 560/175; 549/313; 560/186; 568/862; 568/864; 562/573
[58] Field of Search ................. 560/175, 186; 260/410.9 R, 544 A; 549/313

[56] References Cited

U.S. PATENT DOCUMENTS

| | | | |
|---|---|---|---|
| 3,437,676 | 4/1969 | von Kutepow et al. | 560/114 |
| 3,454,632 | 7/1969 | Mador et al. | 260/544 A |
| 3,457,299 | 7/1969 | Closson et al. | 260/544 A |
| 3,816,488 | 6/1974 | Craddock et al. | 260/413 |
| 3,816,489 | 6/1974 | Craddock et al. | 260/413 |
| 4,245,115 | 1/1981 | Butter | 560/114 |
| 4,414,160 | 11/1983 | Erpenbach et al. | 260/544 A |

OTHER PUBLICATIONS

B. F. Crowe, *Chemistry and Industry*, Jul. 30, 1960, p. 1000.
James E. Huheey, *Inorganic Chemistry* (1983), p. 586.

*Primary Examiner*—Vivian Garner
*Attorney, Agent, or Firm*—Kenneth D. Tremain; Gerald A. Baracka

[57] ABSTRACT

A process is disclosed for forming alkyl 4-oxobutyrates and its acetals which comprises reacting under anhydrous conditions acrolein or its acetals with carbon monoxide and an alcohol of the formula R OH wherein R is lower alkyl in the presence of a catalytically effective amount of a catalyst comprising palladium metal which is either unsupported or supported on an inert carrier and a promoting effective amount of hydrogen halide. An intermediate in the process, i.e., $\beta$-halopropionaldehyde or acetal thereof can also be used in forming alkyl 4-oxobutyrates and acetals thereof by reacting under anhydrous conditions said $\beta$-halopropionaldehyde or its acetals with carbon monoxide and an alcohol of the formula ROH wherein R is lower alkyl in the presence of a catalytically effective amount of a catalyst comprising palladium metal which is either unsupported or supported on an inert carrier.

6 Claims, No Drawings

PROCESS FOR THE PREPARATION OF ALKYL 4-OXOBUTYRATE AND ITS ACETALS

This is a continuation-in-part of U.S. patent application Ser. No. 777,372 filed on Sept. 18, 1985, now abandoned, which is in turn a continuation of U.S. patent application Ser. No. 264,925 filed May 18, 1981, which is now abandoned.

BACKGROUND OF THE INVENTION

This invention relates to a novel process for carbonylation of acrolein to make exclusively linear esters having one additional carbon atom relative to the starting material. More particularly, the present invention is directed to forming alkyl 4-oxobutyrates and acetals thereof from acrolein or its acetals thereof with carbon monoxide and an alcohol under anhydrous conditions in the presence of palladium catalyst promoted with hydrogen halide or from β-halopropionaldehyde or acetals thereof with carbon monoxide and an alcohol under anhydrous conditions in the presence of palladium catalyst. More specifically, the present invention is directed to forming methyl 4-oxobutyrate and its acetals, methyl 4,4-dimethoxybutyrate and gamma-methoxy-gamma-butyrolactone from the catalyzed reaction of acrolein or its methyl acetals thereof, or from β-chloropropionaldehyde or acetals thereof, carbon monoxide and methanol. Methyl 4-oxobutyrate is a useful intermediate in the production of a variety of industrially useful compounds including gamma-butyrolactone, 1,4-butanediol and glutamic acid.

British Patent No. 1,123,367 to von Kutepow, et al., describes a carbonylation reaction in which an olefin is reacted with carbon monoxide and alcohol in the presence of a catalyst such as palladium dichloride bis(triphenylphosphine) to provide a branched carboxylic acid ester. U.S. Pat. No. 4,245,115 to Butter describes a similar carbonylation employing, as a catalyst, a palladium salt complexed with an arsine or stibine ligand, e.g., palladium dichloride bis(tri-phenylarsine) or palladium dichloride bis(tri-p-tolyl arsine).

Craddock, et al. in U.S. Pat. No. 3,816,488 describe a process for the production of isomeric mixtures of linear and branched carboxylic acids through the reaction of ethylenically unsaturated compounds with carbon monoxide and water in the presence of catalyst compositions of rhodium complexes and compounds and an iodide promoter. In U.S. Pat. No. 3,816,489, Craddock, et al. describe a similar process for the production of isomeric mixtures of linear and branched carboxylic acids through the reaction of ethylenically unsaturated compounds with carbon monoxide and water in the presence of catalyst compositions of iridium complexes and compounds and an iodide promoter.

However, the prior art never devised a procedure to convert acrolein or its acetals to exclusively linear products under carbonylation or hydroformylation conditions, although considerable effort and time have been expended. To date, no one has been successful in making the linear products exclusively. Using the prior art methods, acrolein and its acetals produced mixed isomers, i.e., branched and linear isomers, under hydroformylation and carbonylation conditions. For example, as reported by Botteghi, et al. in the Journal of Molecular Catalysis 40, 129–182 (1987), acrolein or its acetals produce both methyl malonaldehyde and succinaldehyde monoacetals under hydroformylation conditions in the presence of carbon monoxide and hydrogen under various catalytic conditions, e.g., cobalt or rhodium catalysts:

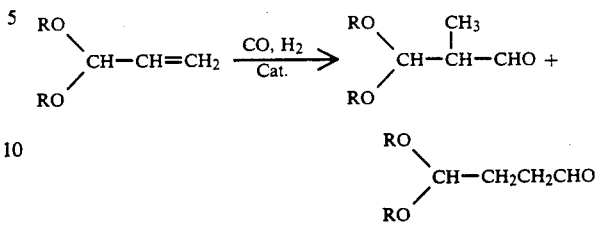

Other investigative groups have also found that under hydroformylation conditions, acrolein or its acetals produced mixed isomers. See, e.g., U.S. Pat. Nos. 4,017,550 to Kummer, 3,963,754 to Cumbo, et al., 3,963,755 to Cumbo, et al. and 3,929,915 to Cumbo, et al. Therefore, using the methods of the prior art it is necessary to find a purification method in order to separate the branched and the linear products.

The process of the present invention overcomes the deficiencies of the prior art. Unlike the prior art, the process of the present invention produces exclusively the linear product. Therefore, under the carbonylation conditions of the present invention, the step requiring the separation of the branched from the linear isomers is eliminated. Consequently, the process of the present invention is more economical and efficient, especially in view of the fact that it is the linear isomer which is used to produce 1,4-butanediol, which is an important material for numerous organic syntheses.

Finally, the process according to the present invention has the advantages of good yields and simplicity.

SUMMARY OF THE INVENTION

This invention relates to a novel process for the carbonylation of acrolein and its acetals to provide linear esters containing one additional carbon atom relative to the starting material. More specifically, the present invention is directed to the process for preparing alkyl 4-oxobutyrate and its acetals, i.e., alkyl 4,4-dialkoxybutyrate and α-alkoxy-α-butyrolactone by reacting acrolein or its acetals thereof under anhydrous conditions with carbon monoxide and an alcohol of the formula ROH where R is lower alkyl in the presence of a catalytically effective amount of a catalyst comprising palladium metal which is either unsupported or supported on an inert carrier and a promoting effective amount of hydrogen halide.

Moreover, the present invention is directed to the process for preparing alkyl 4-oxobutyrates or acetals thereof by reacting β-halopropiopionaldehyde or its acetals under anhydrous conditions with carbon monoxide and an alcohol of the formula ROH where R is lower alkyl in the presence of a catalytically effective amount of a catalyst comprising palladium metal which is either unsupported or supported on an inert carrier.

DETAILED DESCRIPTION OF THE INVENTION

The present invention is directed to the formation of linear alkyl 4-oxobutyrate and its acetals from acrolein or its acetals or β-halopropionaldehyde or its acetals under carbonylation conditions as defined herein. As defined herein, the term "alkyl 4- oxobutyrate and its acetals," refer to alkyl 4-oxobutyrate,

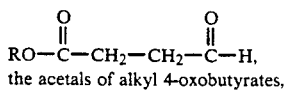

the acetals of alkyl 4-oxobutyrates,

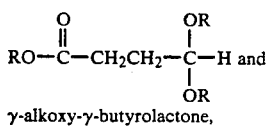

γ-alkoxy-γ-butyrolactone,

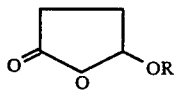

wherein R is lower alkyl.

The term acrolein or its acetals refer to acrolein

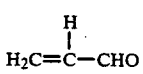

or an acetal of acrolein,

CH₂=CHCH(OR)₂, or

β-alkoxypropionaldehyde ROCH₂—CH₂—CHO, or the acetals of β-alkoxypropionaldehyde, ROCH₂CH₂CH(OR)₂, i.e., 1,1,3-trialkoxypropane, wherein R is as defined hereinabove. The preferred acrolein and its acetals are H₂C=CH—CHO (acrolein) or the dimethyl acetal of acrolein.

The term β-halopropionaldehyde and its acetals refer to β-halopropionaldehyde, X CH₂CH₂CHO, or the acetals of β-halopropionaldehyde, i.e.,

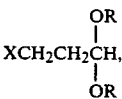

wherein X is halogen and R is as defined hereinabove.

The preferred β-halopropionaldehyde is β-chloropropionaldehyde and the preferred acetal thereof is the dimethyl acetal of β-chloropropionaldehyde.

As used herein, whenever the term lower alkyl is used, alone or in combination with other terms, such as alkoxy, it refers to alkyl groups containing from one to about four carbon atoms. The alkyl groups may be straight-chained or branched and include such groups as methyl, ethyl, propyl, isopropyl, n-butyl, sec-butyl, t-butyl, isobutyl, and the like. The preferred alkyl group is methyl.

The acetals of acrolein, i.e., CH₂=CHCH(OR)₂ are either formed in situ from acrolein, or can be obtained by conventional techniques known in the art. For example, acrolein can be reacted with a lower alkanol of the formula ROH in the presence of a catalytic amount of acid, such as polyphosphoric acid o p-toluenesulfonic acid:

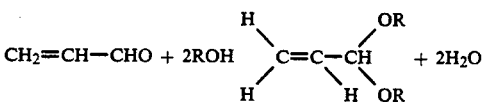

1,1,3-trialkoxy propane can also be prepared in situ or by conventional techniques in the art. For example acrolein can be reacted with a lower alkanol of the formula ROH in the stoichiometric amounts of three moles of ROH to 1 mole of acrolein in the presence of a small amount of acid catalyst as follows:

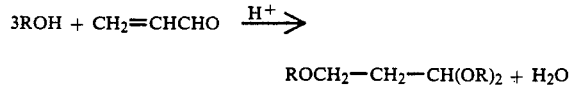

ROCH₂—CH₂—CH(OR)₂ + H₂O

Similary β-alkoxypropionaldehyde can be prepared in situ or by conventional technique known in the art. For example, acrolein can be reacted with a lower alkanol of the formula ROH in the stoichimetric amounts of 1 mole of acrolein to 1 mole of alcohol in the presence of a small amount of acid catalyst as follows:

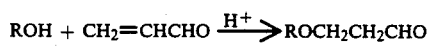

In all of these cases, acrolein is reacted with the alcohol in the absence of solvent or in a suitable solvent, such as benzene, toluene or methylene chloride and in the presence of an acid catalyst, such as a small amount of polyphosphoric acid or p-toluenesulfonic acid. The water that is formed is removed by conventional techniques, such as ordinary distillation, the use of a drying agent (e.g., Al₂O₃ or molecular sieves) or preferably azeotropic distillation.

This general procedure as well as others for the formation of acrolein acetals are discussed in Acrolein, edited by C. W. Smith, John Wiley & Sons, Inc., New York, pp. 128–131 (1962), (hereinafter referred to, as Smith). This portion of the publication as well as the references cited therein are incorporated herein by reference.

The amount of the acetals formed by the processes described hereinabove in Smith is dependent upon the stoichiometric ratio of acrolein to alcohol. In most cases a mixture of two or more of the following products will be formed: the alkyl acetals of acrolein, β-alkoxy-propionaldehyde and 1,1,3-trialkoxypropane. The mixture can be used without purification or separation thereof in the present invention, and the mixtures thereof are also contemplated by the present invention. Therefore, the term acrolein and its acetals, as used herein also refers to the mixture of H₂C=CHCHO, the acetals of acrolein, β-alkoxypropionaldehyde and 1,1,3-trialkoxypropane.

β-Halopropionaldehyde is either commercially available or formed in situ from acrolein or by conventional methods known in the art. For example, hydrogen halide addition to acrolein will form the β-halopropionaldehyde. This reaction is described in Smith, pp. 54–55. This portion of the publication as well as the references cited therein are incorporated herein by reference.

The acetals of β-halopropionaldehyde are commercially available. Moreover, they are formed in situ from acrolein by the process of the present invention. However, when used as a substrate, they can be prepared by conventional techniques known in the art, as for example, by reacting the β-halopropionaldehyde with alcohol in the presence of an acid catalyst, as described in Smith.

The preferred β-halopropionaldehyde and acetals thereof are β-chloropropionaldehyde or the dimethyl acetal thereof.

Again, the amount of β-halopropionaldehyde and acetals thereof formed by conventional methods described in Smith is dependent upon the stoichiometric ratio of acrolein to alcohol and to hydrogen halide. In most cases, a mixture of the β-halo-propionaldehyde or the alkyl acetals thereof will be formed. The mixture can be used without purification or separation thereof in the present invention and the mixtures thereof are also contemplated by the present invention. Therefore, the term β-halopropionaldehyde and its acetals as defined herein also refers to the mixture of β-halopropionaldehyde and the alkyl acetals thereof.

The catalyst used in the present invention is palladium metal. The palladium metal catalyst employed herein is either unsupported or supported upon an inert carrier medium such as alumina, silica, titania, zirconia, carbon, diatomaceous earth, glass beads, ceramic, carborundum and the like. It is preferred that a supported palladium metal catalyst be employed, palladium on alumina or carbon having demonstrated particularly good results.

The palladium metal is incorporated in amounts of from about 0.1 to about 5 percent, preferably from about 0.5 to about 3 percent by weight of the total catalyst. When acrolein or its acetals are used as the substrate, the metal catalyst is employed in the presence of hydrogen halide. The hydrogen halide is believed to act as a promoter in the process of this invention but is ultimately regenerated in situ.

The optimum quantitites of catalyst and acid employed can be readily determined experimentally for a given quantity of acrolein or acetals thereof, carbon monoxide and alcohol and a given set of reaction conditions to achieve a desired reaction rate. The amount of palladium catalyst used is not critical; however, sufficient catalytic amounts are required to obtain a practical reaction rate. The mole ratio of palladium catalyst to acrolein or acetals thereof may range from about 0.001 to about 0.01. It is preferred that the mole ratio ranges from about 0.002 to about 0.008. The most preferred molar ratio is from about 0.003 to about 0.006.

The hydrogen halides used herein are hydrogen bromide, hydrogen chloride or hydrogen iodide. Hydrogen chloride is the preferred hydrogen halide.

The molar ratio of anhydrous halide to acrolein or acetals thereof ranges from about 0.001 to about 0.3, preferably between 0.002 to 0.2, most preferably between 0.04 and 0.1.

However, it is to be noted that the presence of hydrogen halides is not necessary when β-halopropionaldehyde or the acetals thereof are used as the substrate in the present process.

Pure carbon monoxide may be used in the present process. It is, however, also possible to react commercial carbon monoxide which contains inert components, such as saturated hydrocarbons or nitrogen. The stoichiometric amount of carbon monoxide requires at least one mole of carbon monoxide per mole of acrolein or its acetals, or β-halopropionaldehyde or its acetals, but an excess of up to a mole ratio of 10:1 based on the acrolein moiety or β-halopropionaldehyde moiety is advantageous. The preferred molar ratio of carbon monoxide to acrolein or acetals thereof or β-halopropionaldehyde or its acetals range from about 3:1 to about 5:1.

The alcohol, ROH, that is used in the present process is a lower alkanol having 1 to about 4 carbon atoms. The preferred alcohol is methanol. The stoichiometric amount of alcohol required is at least 3 moles of alcohol per mole of acrolein or β-halopropionaldehyde or 1 mole of alcohol per mole of the acetals of acrolein or acetals of β-halopropionaldehyde, but an excess of up to 10 moles of alcohol per mole of acrolein of acetals thereof or β-halopropionaldehyde or acetals thereof can be used. The preferred molar ratio of alcohol to acrolein or acetals thereof or β-halopropionaldehyde or acetals thereof ranges from about 3:1 to about 5:1.

Of course, it is obvious to one skilled in the art that the alkyl groups in the reactants must be identical with that in the products. For example, if methanol is used, the products formed from acrolein under the carbonylation conditions of the present invention will be methyl 4-oxobutyrate and its acetals, i.e., methyl 4,4-dimethoxybutyrate and gamma-methoxy-gamma-butyrolactone. Moreover, in order to avoid transesterification, if an acetal of acrolein is used as the starting material, the "R" group of the acrolein acetal should be identical with the "R" group in the alcohol that is used and in the product that is formed.

The reaction is carried out under anhydrous conditions wherein only dry reagents are used. More specifically, the alcohol that is used is freshly distilled and dried over drying agents, such as molecular sieves. Anhydrous hydrogen halides, such as gaseous, dry hydrogen chloride, which are commercially available, are utilized. The acrolein, the acetals thereof, β-halopropionaldehyde or its acetals that are used are substantially dry. The reaction vessel is purged with nitrogen to remove all water present therein.

In accordance with the present invention, improved yields of alkyl 4-oxobutyrates or acetals thereof are obtained by reaction of the acrolein or acetals thereof, alcohol and carbon monoxide in the presence of a palladium metal catalyst and promoted with hydrogen halide. Moreover, in accordance with the present invention improved yields of alkyl 4-oxobutyrates or acetals thereof are obtained by reaction of the acrolein or acetals thereof, alcohol and carbon monoxide in the presence of a palladium metal catalyst. In both embodiments, the process can be run at temperatures from about 90° C. to about 130° C. and at pressures of carbon monoxide from about 1000 to about 4000 psi, preferably 1350–3500 psi and more preferably 2000–3000 psi, although higher pressures may be utilized.

Besides the carbon monoxide, alcohol, acrolein or acetals thereof, palladium metal catalyst, a polymerization inhibitor capable of stabilizing the acrolein and its acetals may additionally be present. Such polymerization inhibitors include hydroquinones, such as, benzohydroquinone and paramethoxyphenol and the like.

A preferred embodiment of the present invention is the formation of methyl 4-oxobutyrate, and its acetals i.e., methyl 4,4-dimethoxybutyrate, and gamma-methoxy-gamma butyrolactone, which are readily and conveniently produced by the reaction of acrolein or acetals thereof, carbon monoxide and methanol in the presence of palladium metal and hydrogen chloride under anhydrous conditions, according to the present invention.

Without wishing to be bound, acrolein is believed to undergo reaction with alcohol, e.g., methanol, and hydrogen halide (illustrated for hydrogen chloride) to provide beta-chloropropionaldehyde dimethyl acetal as follows:

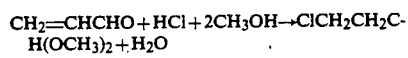

CH$_2$=CHCHO+HCl+2CH$_3$OH→ClCH$_2$CH$_2$CH(OCH$_3$)$_2$+H$_2$O

Carbonylation of the acetal and subsequent methanolysis to provide methyl 4,4-dimethoxybutyrate are thought to proceed as follows:

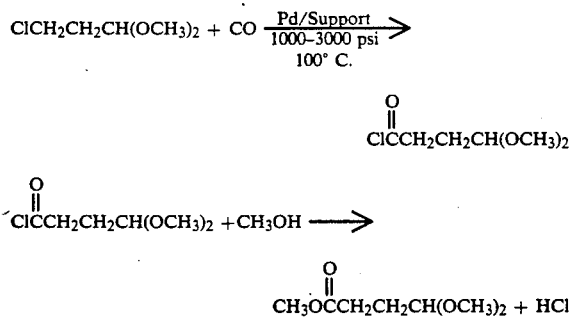

The reaction may also proceed by carbonylation of beta-chloropropionaldehyde, formed by addition of HCl to acrolein, as follows:

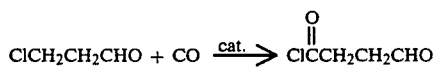

Methanolysis of the acyl chloride provides methyl 4-oxobutyrate:

Further reaction with methanol gives the hemiacetal or dimethyl acetal. The hemiacetal can undergo cyclization to gamma-methoxy-gamma-butyrolactone with elimination of methanol as follows:

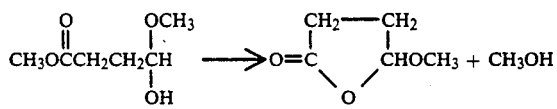

The reaction can be carried out in a flow-trickle phase fixed bed or stirred reactor.

Conventional recovery techniques such as simple distillation can be used to separate the carbonylation products, hydrogen halides and unreacted methanol from the catalyst, thus permitting convenient recycling of the catalyst residue.

Consequently, as shown by the mechanism hereinabove, the methyl 4-oxobutyrate and its acetals are also readily and conveniently produced by the reaction of β-chloropropionaldehyde or methyl acetals thereof, carbon monoxide and methanol in the presence of palladium metal under anhydrous conditions according to the present invention.

Hydrogenation of the products e.g., methyl 4-oxobutyrate, methyl 4,4-dimethoxybutyrate and gamma-methoxy-gamma-butyrolactone employing Raney nickel, ruthenium or palladium on carbon or copper on zinc oxide can be effected in the presence of water and an acid co-catalyst such as para-toluenesulfonic acid to form gamma-butyrolactone. The hydrogenation can also be carried out in the presence of copper chromite to provide 1,4-butanediol.

In a variation of the Strecker reaction disclosed by Huffman, et al., *Chem. Rev.*, 63, 625 (1963) in which the oxo products from methyl acrylate are treated with hydrogen cyanide to form the cyanohydrin, then with ammonia followed by hydrolysis to give glutamic acid, the alkyl-4-oxobutyrates, e.g., methyl 4-oxobutyrate, obtained in accordance with the present invention can be simultaneously or sequentially reacted with hydrogen cyanide and ammonia followed by hydrolysis of the resulting aminonitrile to provide glutamic acid which, in the form of its monosodium salt, is widely used as a food flavor enhancer.

In the foregoing description of the process of the invention where reference is made to acrolein as the substrate, the same process conditions will apply when the acetals of acrolein are used in lieu of acrolein.

The following examples are further illustrative of the process of the invention:

EXAMPLE 1

A 300 ml Hastelloy reactor was provided with a stirrer, a thermocouple and a dip tube for sample withdrawal. Into the reactor was placed 5 g 5% palladium supported on carbon. The reactor was purged with $N_2$ and charged with 100 ml solution containing 29.2 g acrolein (97% purity), 50.1 g methanol and 1.7 g anhydrous hydrogen chloride. The reaction solution was previously prepared by dropwise addition of acrolein to a stirred methanol solution of hydrogen chloride while being maintained at 35°–40° C. The reactor was pressurized with carbon monoxide to 2400–2900 psi, sealed and heated at 99°–106° C. with stirring. A sample was withdrawn after one hour reaction time and analyzed by gas chromatography coupled with mass spectrometry. The analyses showed that the products were: methyl 4-oxobutyrate, methyl 4,4-dimethoxybutyrate and gamma-methoxy-gamma-butyrolactone. No branched isomers were detected in the reaction mixture. An aliquot of the above sample was analyzed for ester content (measure of carbonylation) by room-temperature saponification after neutralization of free HCl at 0° C. The analysis indicated an acrolein conversion of 48.5% at 56.4% selectivity to $C_4$ esters expressed as methyl 4-oxobutyrate. Analyses of an additional sample taken after two hours of reaction time indicated a conversion of 69.3% at 52.8% selectivity.

EXAMPLE 2

Example 1 was repeated except that 0.1 g of hydroquinone was added to the reaction mixture. At one hour, the acrolein conversion was 58.2% at 70.7% selectivity changing to 83.5% and 49.7%, respectively, at two hours of reaction time. These results indicate that use of a polymerization inhibitor initially increased the selectivity to methyl 4-oxobutyrate.

EXAMPLE 3

A 70 ml Hastelloy pressure reactor was charged with 0.5 g of 5% palladium on alumina, 5 ml acrolein (97% purity) and 15 ml methanol solution containing 1.49 g anhydrous hydrogen chloride. The reactor was pressurized with carbon monoxide to 3000 psig, sealed and shaken in a heated oven at 100° C. for 6 hours. After cooling to room temperature, the reactor was slowly vented to atmospheric pressure and the reaction mixture was filtered. Analysis of the filtrate by gas chromatography coupled with mass spectrometry showed formation of methyl 4-oxobutyrate ($OCHCH_2CH_2COOCH_3$), as the major product with small amounts of its acetals: methyl 4,4-dimethoxybutyrate [(CH₃O)₂CHCH₂CH₂COOCH₃] and gamma-methoxy-gamma-butyrolactone

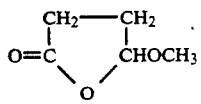

No branched isomers were detected in the reaction mixture.

EXAMPLE 4

A solution of 8.6 g acrolein dimethyl acetal and 0.9 g anhydrous hydrogen chloride dissolved in 8.0 ml methanol is placed in a 70 ml Hastelloy pressure reactor containing 0.5 g of 5% palladium supported on alumina. The reactor is pressurized with carbon monoxide to 3500 psi, sealed and shaken at 90° C. for two hours. The reactor is cooled, the contents filtered and the filtrate is subjected to flash distillation in vacuo condensing the volatile materials at −80° C. Analysis of the condensate shows formation of methyl 4,4-dimethoxybutyrate without evidence of branched isomers.

EXAMPLE 5

Example 3 is repeated except that 1,1,3-trimethoxypropane is used instead of acrolein. Thus, a 2.0 ml sample of reagent grade 1,1,3-trimethoxypropane, 6 ml methanol and 0.12 g anhydrous hydrogen chloride is carbonylated according to the procedure of Example 3 using 0.08 g of 5% Pd on alumina. Analysis shows formation of methyl 4,4-dimethyoxybutyrate and a small amount of methyl 4-oxybutyrate with no evidence of branched isomers.

EXAMPLE 6

3-Chloropropionaldehyde dimethyl acetal was prepared as follows: Into a 500 ml round bottom flask provided with a magnetic stirrer were placed 175 ml chloroform, 33 ml acrolein and 40 ml methanol. The solution was cooled to −15° C. (dry ice-carbon tetrachloride), and anhydrous hydrogen chloride was bubbled into it with stirring, allowing the temperature to rise to 5° C. The reaction mixture, stored in a freezer overnight, resulted in separation into two layers. The lower layer was removed and treated with an aqueous solution containing sodium bicarbonate to neutralize free hydrogen chloride, washed with distilled water and dried with magnesium sulfate. The solution was distilled under vacuum giving a main fraction having a vapor pressure of 30 mm of mercury at 60° C. Analysis indicated that the mixture consisted of about equal parts of 3-chloropropionaldehyde dimethyl acetal and 3-chloropropionaldehyde.

A 10 ml aliquot of the above mixture together with 10 ml of methanol was carbonylated according to the procedure of Example 3. Analysis indicated formation of methyl 4,4-dimethoxybutyrate as the major product with smaller amounts of methyl 4-oxobutyrate and α-methoxy-α-butyrolactone with no evidence of branched isomers.

The following comparative examples demonstrate that the conditions of the present invention are critical to the efficacy of the carbonylation reaction.

Comparative Examples 1 and 2 demonstrate the criticality of performing the reaction condition pursuant to the present invention under anhydrous conditions. As clearly shown by Comparative Examples 1 and 2, when aqueous hydrohalic acid, such as aqueous hydrochloric acid, replaces dry hydrogen halide, e.g. anhydrous hydrogen chloride, the yields of the desired products are reduced considerably relative to that produced according to the present invention. Moreover, unlike the present invention, a side-product, a dark brown viscous liquid or black brown solid, is also formed under hydrous conditions. Thus, in order to maximize yields and minimize the formation of side products, the present invention is run under anhydrous conditions.

COMPARATIVE EXAMPLE 1

A 70 ml Hastelloy pressure reactor provided with a glass liner was charged with 0.5 g of 5% palladium/carbon, 1.41 ml aqueous concentrated hydrochloric acid, 10 ml methanol, followed by drop-wise addition of 5 ml reagent grade 97% purity acrolein, while holding the mixture at 35°–40° C. during the addition under nitrogen cover. The reactor was pressurized at room temperature with carbon monoxide to 3500 psig, sealed and shaken in a heated oven at 103° C. for one hour. After cooling, the reactor was vented to atmospheric pressure and the reaction mixture was filtered and the filtrate subjected to flash distillation in high vacuum (10⁻⁴ mm Hg) overnight, condensing the volatile materials in a U-tube held at −78° C. (dry ice) and, leaving behind a nonvolatile residue. Analysis of the condensate by gas chromatography and ester number determination showed formation of 0.55 gram methyl 4-oxobutyrate (4.5 mmoles) amounting to a yield of 6.2% based on charged acrolein. The nonvolatile residue weighing 3.92 grams was a dark-brown viscous liquid

COMPARATIVE EXAMPLE 2

Comparative Example 1 was repeated except that 3.00 ml of aqueous 5.472 N hydriodic acid (16.5 mmoles HI) were used instead of hydrochloric acid. Analysis of the −78° C. condensate showed formation of 0.67 gram of methyl 4-oxobutyrate (5.8 mmoles) corresponding to a yield of 8.0% based on charged acrolein. The nonvolatile residue weighing 2.55 g was a black-brown solid.

The following Comparative Examples 3–6 compare the present invention with that described in U.S. Pat. No. 3,816,488 to Craddock, et al. As indicated hereinabove, carbonylation of alkenes under the Craddock et al. system produces a mixture of linear and branched isomers; their system does not produce solely the linear isomers. On the other hand, carbonylation of acrolein under the reaction conditions of the present invention produces exclusively linear product, e.g., methyl 4-oxobutyrate, in good yields. As clearly shown by the following comparative examples acrolein is a poor substrate under Craddock, et al. reaction conditions. The data herein clearly shows that the present invention is unexpectedly more effective than the Craddock, et al. system when acrolein is used as the substrate. Moreover, based on the results of the following comparative examples, one skilled in the art readily concludes that a catalyst containing palladium metal is more effective than catalysts containing other Group VIII metals, such as rhodium used by Craddock, et al. Furthermore, the following comparative examples clearly show that, unlike the present invention, acrolein forms a polymerized side product under Craddock, et al. conditions.

COMPARATIVE EXAMPLE 3

Comparative Example 1 was repeated except that 0.062 g of RhCl$_3$·3H$_2$O (0.236 mmoles) were used instead of Pd/carbon. Analysis of the −78° C. condensate showed formation of 0.27 gram of methyl 4-oxobutyrate (2.3 mmoles) corresponding to a yield of 3.2% based on charged acrolein. The nonvolatile residue weighing 2.52 g was a black solid (polymer).

COMPARATIVE EXAMPLE 4

Comparative Example 3 was repeated except that 3.00 ml of aqueous 5.472 N hydriodic acid (16.5 mmoles HI) was used instead of hydrochloric acid. Analysis of the −78° C. condensate showed formation of 1.00 g of methyl 4-oxobutyrate (8.6 mmoles) corresponding to a yield of 10.9% based on charged acrolein. The nonvolatile residue weighing 3.96 g was a black solid (polymer).

COMPARATIVE EXAMPLE 5

A stainless steel pressure reactor provided with a glass liner, flushed with nitrogen, was charged with a 10 ml methanol solution containing 0.073 g (0.28 mmoles) RhCl$_3$·3H$_2$O and 0.13 ml of 55 wt % aqueous hydrogen iodide (0.98 mmoles), and 4.30 g (76.9 mmoles) freshly distilled acrolein. The reactor was pressurized with 2200 psig carbon monoxide, sealed, and heated in an air oven at 104° C. while shaken for one hour. After cooling to room temperature, the reactor was chilled with dry ice and slowly vented to atmospheric pressure. The reaction mixture was distilled in a vacuum line condensing the volatile material in a trap cooled with liquid nitrogen. Ester number determination in the condensate showed the presence of 3.31 mmoles of ester. The nonvolatile viscous material weighed 1.48 g, assumed to be polymeric acrolein (26.43 mmoles). These results indicate that 38.7% of the acrolein was converted to 11.1% ester and 88.9% undesirable polymeric material.

COMPARATIVE EXAMPLE 6

Comparative Example 5 was repeated except that 0.1 g of benzohydroquinone was added as a polymerization inhibitor. The results showed formation of 5.9 mmoles of ester and 1.33 g of viscous non-volatile residue (23.8 mmoles of acrolein polymer) indicating that 38.6% of acrolein was converted to 19.9% of ester and 80.1% of undesirable polymeric material, despite the presence of a polymerization inhibitor.

The above preferred embodiments and examples are given to illustrate the scope and spirit of the present invention. These embodiments and examples will make apparent to those skilled in the art other embodiments and examples. These other embodiments are examples within the contemplation of the present invention. Therefore the present invention should be limited only by the appended claims.

What is claimed is:

1. A process for forming alkyl 4-oxobutyrates and acetals thereof which comprises reacting under anhydrous conditions β-halopropionaldehydes or the acetals thereof, carbon monoxide and an alcohol of the formula ROH wherein R is lower alkyl in the presence of a catalytically effective amount of a catalyst comprising palladium metal which is either unsupported or supported on an inert carrier.

2. The process according to claim 1 wherein β-halopropionaldehyde or the acetals thereof are β-chloropropionaldehyde or the alkyl acetals thereof.

3. The process according to claim 2 wherein methyl 4-oxobutyrate and its acetals are formed by reacting under anhydrous conditions β-chloropropionaldehyde dimethyl acetal, carbon monoxide and methanol in the presence of a catalytically effective amount of a catalyst comprising palladium metal which is either unsupported or supported on an inert carrier.

4. The process according to claim 1 wherein a polymerization inhibitor is additionally present.

5. The process according to claim 4 wherein the polymerization inhibitor is benzohydroquinone or paramethoxyphenol.

6. The process according to claim 1 wherein the inert support is alumina or carbon.

* * * * *